United States Patent [19]

Gregory

[11] 4,071,023

[45] Jan. 31, 1978

[54] RESTRAINING DEVICE

[76] Inventor: Peter J. Gregory, 1301 Allen St., Aliquippa, Pa. 15001

[21] Appl. No.: 722,367

[22] Filed: Sept. 13, 1976

[51] Int. Cl.[2] .......... A61F 13/00

[52] U.S. Cl. .......... 128/133; 70/16

[58] Field of Search .......... 128/132-135; 70/16, 18

[56] References Cited

U.S. PATENT DOCUMENTS

| | | | |
|---|---|---|---|
| 2,059,563 | 11/1936 | Donoghue | 128/134 |
| 2,650,590 | 9/1953 | Moore et al. | 128/134 |
| 2,706,477 | 4/1955 | Daake | 128/134 |
| 2,895,471 | 7/1959 | Rollie | 128/133 |
| 3,042,032 | 7/1962 | Vogel | 128/134 |
| 3,426,559 | 2/1969 | Schubach et al. | 70/16 |
| 3,467,085 | 9/1969 | Cormier | 128/83 |
| 3,474,781 | 10/1969 | Gaylord | 128/134 |
| 3,516,124 | 6/1970 | Merser | 24/16 |
| 3,621,681 | 11/1971 | Mikesic | 70/16 |
| 3,812,852 | 5/1974 | Kohvalin | 128/134 |

*Primary Examiner*—Lawrence W. Trapp

*Attorney, Agent, or Firm*—Arnold B. Silverman

[57] ABSTRACT

A restraining device having an elongated body portion and a pair of arms extending outwardly from the body portion. Each of the arms of such position on the body portion and of such length as to cooperate with one end of the body portion in establishing a closed loop. Locking means, which may be adjustable, are provided for resisting opening of the loop. The restraining device may be of unitary construction and may be molded as a unit from a material such as a resinous plastic.

12 Claims, 10 Drawing Figures

RESTRAINING DEVICE

BACKGROUND OF THE INVENTION

1. Field of the Invention

This invention relates to a restraining device adapted for use on humans, as well as animals, and, more specifically, this invention relates to multiple loop restraining devices which may be employed in lieu of handcuffs and other restraining devices presently employed.

2. Description of the Prior Art

In conventional use, for many decades, the handcuffs employed by law enforcement officers have consisted of a pair of metal loop forming members which are adapted to be secured in the locked position by means of a separately formed metal lock which requires the use of a key to open the same. Several problems have occurred in connection with the use of such conventional devices. First of all, occasionally in the process of subduing a struggling individual, a law enforcement officer has succeeded in securing one cuff around the wrist of the individual, who in turn, by swinging the arm to which the cuff has been secured, may use the loose metal cuff as a weapon to injure the officer and third parties. A further problem has been the need to carry one or more of the rather bulky and heavy sets of handcuffs in order that the police officer may be properly equipped to apprehend one or more individuals. There has been the further need to have available the appropriate key when it is desired to free the restrained individual.

The above-described problems have not only been experienced by law enforcement officers, but also by others where restraining means are needed, such as in connection with military uses, hospital patients and other persons and animals requiring restraint.

There has also been lacking a restraining device which not only did not have the disadvantages of the conventional metal handcuffs, but also permitted adjustable locking so that each loop may individually be locked in a number of positions corresponding to different loop sizes.

U.S. Pat. No. 3,426,559 discloses a restraint device made of a flexible cord wherein one end is provided with an integrally formed eyelet which receives another portion of the cord to define a first loop, and the other end is provided with a metal eye which is adapted to snap over the cord to define a second loop. The approach of this disclosure not only fails to provide for loops which may be locked in a fixed position, it fails to provide for any sort of locking device which would preclude enlargement of the loop so as to permit the restrained individual to free himself.

It has also been known to provide various types of flexible belt restraints which require prolonged and cumbersome effort in securing the restraint to an individual. See, for example, U.S. Pat. Nos. 2,706,477 and 3,812,852.

U.S. Pat. No. 3,621,681 discloses a pair of generally G-shaped restraints secured to an elongated handle. The leg restraint of this disclosure is adapted to be employed in combination with some sort of hand restraint.

It has also been known to provide an elastic band connected at opposed ends to looped forming members which are provided with snap elements. See U.S. Pat. No. 2,650,590. This disclosure is said to be designed for infant restraint in such fashion as to permit walking but not climbing. The elastic band, however, would permit undesired freedom in connection with most uses of restraining devices by law enforcement officers, hospital authorities and the like. Also, apart from possible use with infants, the snaps would not provide effective restraint against undesired loop opening by adults and many types of animals.

U.S. Pat. No. 3,042,032 discloses a form of baby restraint involving an elongated endless rubber band and two clip members which serve to define the degree of opening of loops formed within the band. Not only does this disclosure provide for objectionable elasticity between the loops, but also it is not adapted for ready use against a struggling individual.

There remains, therefore, a substantial need for an efficient, economical and less hazardous means for restraining individuals and animals. In addition, there remains the need for such a restraining device wherein the device is adapted for adjustable locking of the loops, requires no key to free the individual or animal, but rather is adapted for destructive removal and may be used efficiently on a resisting individual or animal.

SUMMARY OF THE INVENTION

The above-described needs have been met by the restraining device of the present invention. The restraining device of this invention preferably has an elongated body portion and a pair of arms extending outwardly from the body portion. Each arm is adapted to cooperate with an end portion of the body so as to define a closed loop, and locking means are provided, preferably integrally, to permit locking in a number of adjustable positions. In one preferred form of the invention the restraining device may consist of a unitary molded article. Resinous plastic materials, for example, which are flexible under the influence of bending forces but resistant to substantial elongation under the influence of tension forces are suitable for use in this invention.

It is an object of the present invention to provide an economically producible, lightweight restraining device which is adapted for ready use on a wide range of individuals and animals for temporary or long-term restraint.

It is another object of this invention to provide such a restraining device which may readily and safely be secured in a number of adjustable, locking looped positions even against an individual or animal which is resisting such restraint.

It is another object of this invention to provide such a restraining device which may be opened only through permanent destruction of the closed loops.

These and other objects of the invention will be more fully understood from the following description of the invention on reference to the illustrations appended hereto.

DESCRIPTION OF THE PREFERRED EMBODIMENTS

As used herein, the term "restraining device" shall refer to articles having at least two loop forming portions and being adapted to restrain humans or animals. This term shall expressly include, but not be limited to, articles which are adapted to restrain human limbs, such as handcuffs and leg restraints. It shall also include, but not be limited to, articles having one or more loop forming elements adapted to be secured to portions of humans or animals, and one or more loops adapted to be secured to some sort of restraining member such as a pole, post or tree, for example.

Figure 1:
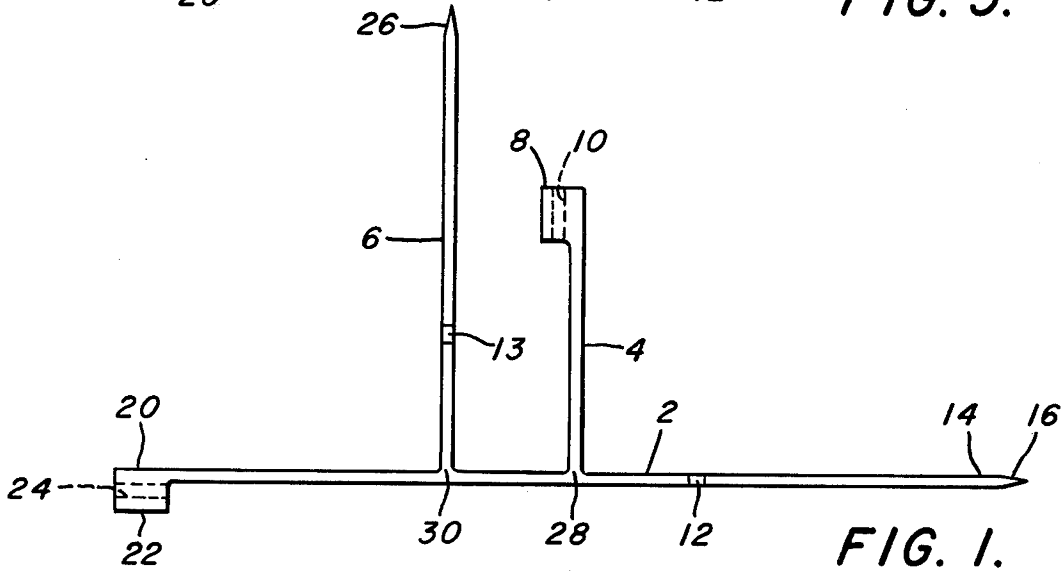
FIG. 1 is a front elevational view of one embodiment of the present invention.

Referring now more specifically to FIG. 1, there is shown a form of restraining device of the present invention. It is seen that the restraining device has a body portion 2, a first transversely outwardly projecting arm 4 and a second generally transversely outwardly projecting arm 6. Arm 4 has an integrally formed female member 8 which is provided with an elongated bore 10. Female member 8 is adapted to cooperate with end 14 of body portion 2 in such fashion that end 14 serves as a male member which extends into bore 10 of female member 8 in interlocked relationship to establish a first loop. It is noted, in the form shown, that end 14 terminates in a pilot surface 16 which facilitates insertion of end or male member 14 into the bore 10 of female member 8. Similarly, end 20 of body portion 2 has a female member 22 provided with an elongated bore 24. The free end 26 of arm 6 serves as a male member which cooperates with end 20 of body portion 2 to define a second loop with male member or end 26 having a pilot surface which facilitates insertion of arm 6 into bore 24.

Figure 2:
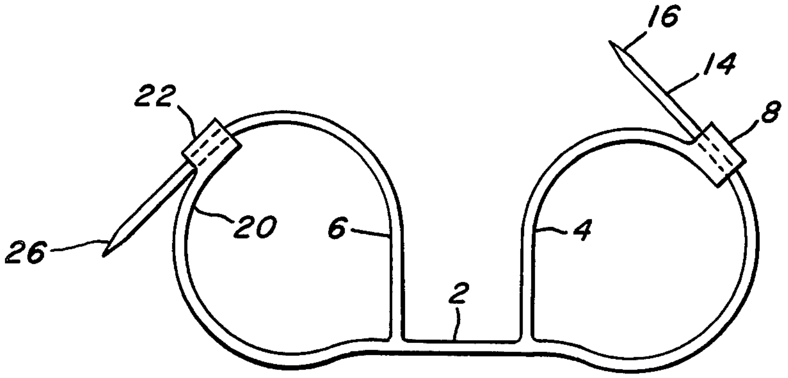
FIG. 2 is a front elevational view of the restraining device of FIG. 1 showing the device in a closed position.

In the form shown in FIGS. 1 and 2, bore 10 is narrower than the adjacent portion of body 2. End 14 is produced with a reduced width to facilitate insertion thereof into the bore. Transition region 12 separates the narrower end 14 from the wider portion of body 2. Similarly, transition 13 separates the upper narrower portion of arm 6 from the lower portion thereof.

Referring still to FIG. 1, it is noted that arms 4, 6 project generally transversely outwardly from body portion 2 and are connected to body portion 2 at locations 28 and 30 which are spaced inwardly from ends 16, 20, respectively, of the body portion 2 and are spaced from each other. The center-to-center spacing between arms 4, 6 for handcuff use is preferably about 1 to $2\frac{1}{2}$ inches.

Referring now to FIG. 2, the restraining device of FIG. 1 is shown in closed position. Arm 4 which bears female member 8 is shown in locked relationship with respect to male member 14 to thereby define a first closed loop. Similarly, arm 6 cooperates with female portion 22 of end 20 to define a second closed loop. As will be described hereinafter, in a preferred form of the invention, the locking means which retain the loops in the desired dimensions and resist opening thereof are preferably adjustable so as to permit locking at several different loop sizes.

Figure 3:
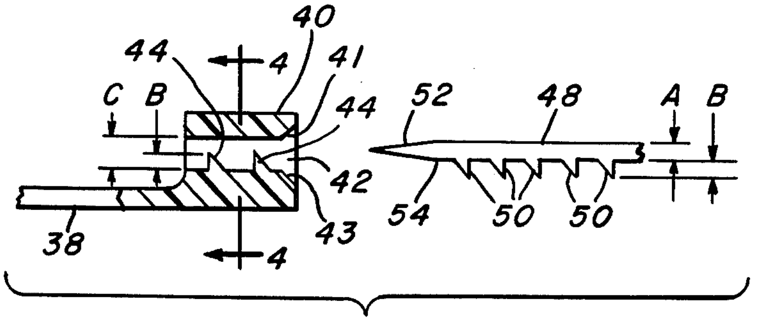
FIG. 3 is a fragmentary illustration of one form of adjustable locking means contemplated by the present invention.
Figure 4:
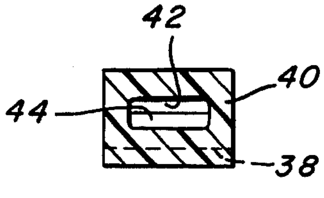
FIG. 4 is a cross-sectional view of a female component of a locking device taken through 4—4.

Referring now to FIGS. 3 and 4, the details of one form of adjustable locking device will now be considered. As is shown in FIG. 3, a loop forming member 38 which may either be an end portion of a body portion or an arm member is provided with a female member 40 having a bore 42 therethrough. The bore which has a height "C" contains, in the form shown, two upwardly projecting ribs 44 defining a recess therebetween. Pilot surfaces 41, 43 facilitate insertion of male member 48 into bore 42. A male member 48 which may be a body portion end or arm has a number of downwardly directed ribs 50 defining recesses therebetween. The thickness of the male member 48 exclusive of ribs 50 is indicated by the dimension "A" and is preferably no greater than the dimension "C" minus "B" (the latter is the height of rib 44) so as to permit free entry of male member 48 into female member 40 except for the interaction between ribs 44 and 50. It is noted that each rib 44 has the surface most remote from the male member 48 oriented generally perpendicularly with respect to the connected bore defining surface of female member 40. The other surface of ribs 44 slopes generally rearwardly and inwardly with respect to the forward portion of bore 42. Similarly, ribs 50 have a surface disposed farthest from pilot surface 52 oriented generally perpendicularly with respect to the lower surface 54 of male member 48 and the other surface oriented generally angularly downwardly and away from pilot surface 52. In a preferred form of the invention, the angular orientation of the two sloped surfaces on ribs 44 and 50 will be generally complementary. In this fashion it will be appreciated that as male member 48 is introduced into bore 42, the sloping surfaces of ribs 44, 50 will interengage and be conducive to further insertion. It will be appreciated that as soon as the rib 50 disposed closest to pilot surface 52 engages the forwardmost of ribs 44, the sloped surfaces will permit relatively easy movement of rib 50 over rib 44. A ratchet effect is, however, provided as the two perpendicular surfaces of the first two ribs 44, 50 will thereupon engage and resist relative separating movement of the male member 48 from the female member 40. At this point a first loop size which is the largest diameter locked loop for the particular article has been established. It will be appreciated that in similar fashion, by further insertion of male member 48 into female member 40, the dimension of the loop is reduced and successive locking engagements will be established between ribs 44 and 50. As a result, one employing the restraining device need merely insert the male member 48 into the female member 40 until the desired locked position has been reached. Automatic resistance to opening of the loop is provided by the locking system.

Figure 5:
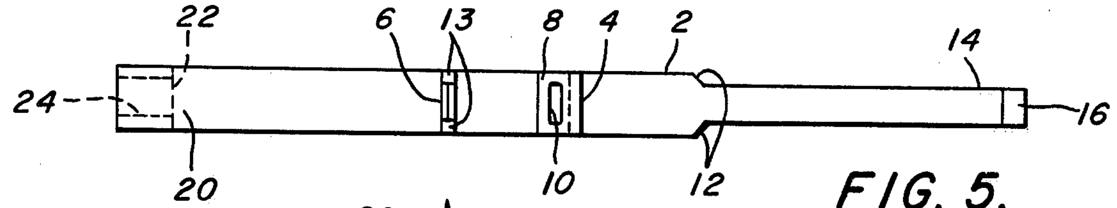
FIG. 5 is a top plan view of the restraining device shown in FIG. 1.

FIG. 5 illustrates a top plan view of the restraining device illustrated in FIG. 1. It will be appreciated that in the form shown, the locking device body portion 2 has a width which is substantially greater than its thickness, and arms 4, 6 have a width which is generally coextensive with the width of body portion 2 except for the portion of arm 6 disposed above transition 13.

In order to provide additional information regarding the present invention, an illustrative example of a specific embodiment intended for use in an adult handcuff will be considered. An article having the appearance of the embodiment of FIG. 1 is molded as a unit from polyethylene. Body portion 2 has a thickness of about 1/16 inch, the spacing between arms 4, 6 is 1¾ inch, and arms 4, 6 are of 4 inches and 7 inches length, respectively. Arm 6 is 4 inches from the free end at 20, and arm 4 is 7 inches from the free end at 16. Bore 24 is one-half inch long.

The exterior surfaces of the restraining member are preferably of rough surface texture in order to facilitate manual engagement thereof by the user. In plastic elements, the roughness may advantageously be molded into the surface.

It will be appreciated that in the preferred illustrated embodiments of the invention, shown in FIGS. 1 through 5, the restraining device has advantageously been made as a unitary molded article, thereby eliminating the need for assembly of a number of components either at the factory or in use. The restraining device is preferably made from a resinous plastic material which is relatively flexible when subjected to bending forces, but is resistant to substantial elongation upon the imposition of tensile forces. Among the preferred materials for this use are polyvinyl chloride, polyethylene, polypropylene, polyester and fiber, filament or whisker reinforced thermosetting resins.

Figure 7:
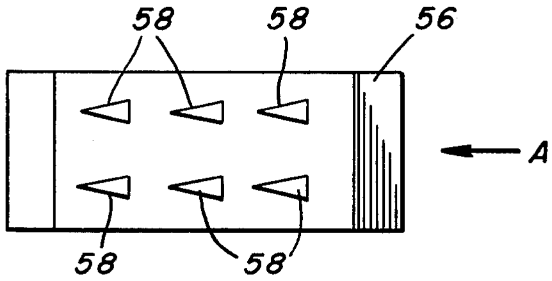
FIG. 7 is a top plan view of the locking means portion of FIG. 6.
Figure 6:
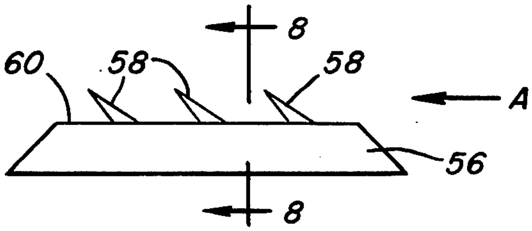
FIG. 6 is a front elevational view of a portion of a modified locking means of the present invention.
Figure 8:
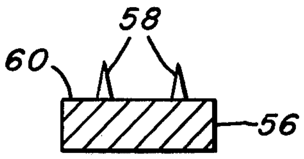
FIG. 8 is a cross-sectional view of the locking means portion of FIG. 6 taken through 8—8.
Figure 9:
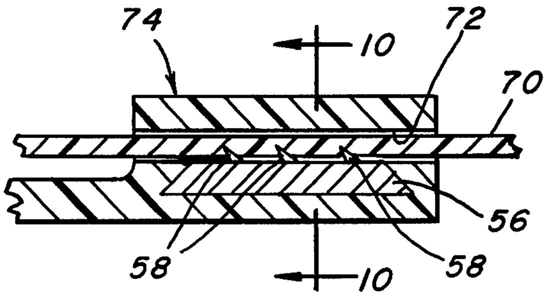
FIG. 9 is a cross-sectional illustration of a locking joint employing the locking means of FIGS. 6 through 8.
Figure 10:
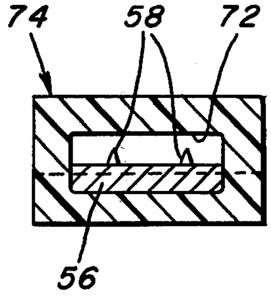
FIG. 10 is a cross-sectional illustration of the locking joint of FIG. 9 taken through 10—10.

Referring now to FIGS. 6 through 10, a modified embodiment of the invention will be considered. In this form, a separately formed locking means component is employed. As is shown in FIGS. 6 through 8, in the form shown, the locking member may advantageously be made as a unitary, substantially rigid article from a material such as rigid plastic, rubber, steel or aluminum, for example. The locking element has a base 56 and a number of upwardly tapered, angularly disposed, integrally formed spikes 58. In this form the direction of entry of the male member is indicated by arrow "A". The angle of inclination of spikes 58 with respect to upper surface 60 is such as to facilitate insertion of a male member in direction "A", but resist removal thereof. In this form, the male member may have a generally flat lower surface to be engaged by spikes 58 as is shown in FIGS. 9 and 10, wherein male member 70 is received within bore 72 of female member 74. The spikes 58 are shown in FIG. 9 engaging male member 70 to resist withdrawal thereof from bore 72. This embodiment permits a more refined gradation of adjustable locking positions.

The locking element 56 may be secured in place by molding adhesive bonding, friction fit or other effective means.

It will therefore be appreciated that the present invention provides a lightweight, restraining device which may advantageously be molded as a unitary article and is readily secured to a human being or animal to be restrained. Once the loops have been fixed in the locked position, opening of the loops is resisted in any fashion except by the use of means which physically destroy the loop integrity as distinguished from relative separation of the loop forming elements. In general, the materials will be selected in such fashion that the use of some sort of tool will be required to free the restrained portion of the body. For example, it is contemplated that an individual having the restraining device employed as handcuffs could not, in any fashion, sever either body portion 2 between the two loops (FIG. 2) or the loops themselves, but that an individual with a suitable instrument, such as a policeman with a pair of scissors could readily free the individual. It will further be appreciated that the restraining device may advantageously and economically be manufactured by unitary molding from a resinous plastic material. The restraining device is sufficiently lightweight that the risk of its being used as a dangerous weapon by the one sought to be restrained is virtually non-existent. All of these advantages are accomplished in an economical fashion so as to permit ready disposal of the restraining device after use has been completed and also permits a law enforcement officer or other user to carry a number of them without any burdensome weight or bulk making such multiple supply unpleasant.

While certain preferred embodiments of the present invention have been specifically disclosed herein, the invention is not so limited, and many variations will occur to those skilled in the art. For example, the bore of the female member has been shown as being oriented generally parallel to the longitudinal axis of the arm or body portion on which it is mounted. The bore may, however, be oriented angularly or transversely with respect to such axis if desired. Also, it will be appreciated that the distance between arms 4, 6 (taken from center to center along body 2 in FIG. 1) may be varied depending upon the particular need of the specific restraint. Also, while the arms are shown as projecting generally perpendicularly with respect to the body 2, and being one of each type, it will be appreciated that the arms may project angularly with respect to the body, be both male or both female, or project on different sides of the body if desired, for example.

Whereas, particular embodiments of the invention have been described above for purposes of illustration, it will be evident to those skilled in the art that numerous variations of the details may be made without departing from the invention as defined in the appended claims.

I claim:

1. A restraining device comprising,
an elongated unitary body portion,
a pair of arms extending outwardly from said body portion, each said arm being of such length and position on said body portion as to cooperate with one end of said body portion in establishing a closed loop,
locking means for resisting opening of said closed loop, and
said locking means having means for permanently resisting loop enlargement so as to preclude substantial loop enlargement without permanent destruction of said loop, and
said locking means having adjustable means providing a number of different locking positions corresponding to different loop sizes, whereby
each of said loops will be partially defined by said body portion, partially defined by one said arm and will be permanently secured by said locking means.

2. The restraining device of claim 1 including,
the length of said body portion between the centers of the two locations where said arms are connected thereto being about 1 to 2½ inch.

3. A restraining device comprising,
an elongated body portion,
a pair of arms extending outwardly from said body portion, each said arm being of such length and position on said body portion as to cooperate with one end of said body portion in establishing a closed loop, locking means for resisting opening of said closed loops, said locking means having adjustable means providing a number of different locking positions corresponding to different loop sizes, and said arms extending generally transversely outwardly from said body portion.

4. The restraining device of claim 3 including, said arms being connected to said body portion at positions spaced from the ends of said body portion.

5. The restraining device of claim 4 including, said adjustable means including interengaging formed portions of said male and female members.

6. The restraining device of claim 5 including, said formed portions including projecting teeth on one of said male and female members, and teeth receiving recesses on the other said male and female members.

7. A restraining device comprising, an elongated body portion, a pair of arms extending outwardly from said body portion, each said arm being of such length and position on said body portion as to cooperate with one end of said body portion in establishing a closed loop, locking means for resisting opening of said closed loops, said locking means having adjustable means providing a number of different locking positions corresponding to different loop sizes, said restraining device composed of resinous plastic.

8. A restraining device comprising, an elongated body portion, a pair of arms extending outwardly from said body portion, each said arm being of such length and position on said body portion as to cooperate with one end of said body portion in establishing a closed loop, locking means for resisting opening of said closed loops, said locking means having adjustable means providing a number of different locking positions corresponding to different loop sizes, said locking means including one of said cooperating loop defining arms and body ends serving as a female member having an opening for receipt of the other of said cooperating loop defining arms and body ends which serve as a male member, whereby the size of said loop is reduced as said male member is extended into said female member opening.

9. The restraining device of claim 8 including, one said female member being formed on one said body portion end, and the other said female member being formed on a said arm.

10. A restraining device comprising, an elongated body portion, a pair of arms extending outwardly from said body portion, each said arm being of such length and position on said body portion as to cooperate with one end of said body portion in establishing a closed loop, locking means for resisting opening of said closed loops, said locking means having adjustable means providing a number of different locking positions corresponding to different loop sizes, said restraining device being of unitary construction, and said arms in undeformed position being oriented generally perpendicularly with respect to said body portion.

11. The restraining device of claim 8 including, a locking element secured within said female member and having a plurality of spikes disposed within said female member opening.

12. The restraining device of claim 11 including, said spikes projecting generally angularly toward the direction of movement of said male member as it enters said female member opening.

* * * * *